US006395721B1

(12) United States Patent
Robinson et al.

(10) Patent No.: US 6,395,721 B1
(45) Date of Patent: May 28, 2002

(54) LOW POTENCY UNPRESERVED STERILE TOPICAL CORTICOSTEROID COMPOSITIONS FOR DERMATITIS

(75) Inventors: Howard N. Robinson, Lutherville; Neil F. Martin, Potomac, both of MD (US)

(73) Assignee: Leonard Bloom, Towson, MD (US); a part interest ( * ) Notice: Subject to any disclaimer, the term of this patent is extended or adjusted under 35 U.S.C. 154(b) by 0 days.

(21) Appl. No.: 09/477,838

(22) Filed: Jan. 5, 2000

(51) Int. Cl.⁷ .............................................. A61K 31/56
(52) U.S. Cl. ....................................... 514/177; 514/912
(58) Field of Search .................................. 514/177, 912

(56) References Cited

U.S. PATENT DOCUMENTS

| | | | |
|---|---|---|---|
| 3,348,905 A | 10/1967 | Reveley | 21/56 |
| 4,797,402 A | 1/1989 | Dorsey | 514/171 |

OTHER PUBLICATIONS

Sirbu et al—Chemical Abstracts vol. 100: abstract 56870; (1982).

Dorsey—Chemical Abstracts vol. 110 abstract 121459e (1989).

Tuomi et al—Chemical Abstracts vol. 114 abstract 192384v (1991).

Zilberman et al—Chemical Abstracts vol. 84 abstract 140734b (1975).

Maistrello et al—Chemical Abstracts vol. 80 abstract 22968a (1974).

Alexander A. Fisher, M.D., "Contact Dermatitis" Third Edition; 1986; Lea & Febiger–Philadelphia; pp. 77, 893 and 913.

Maistrello et al—Quantitative Effect of Topically Applied Anti–Inflammatory Agents on External Ocular Inflammation in Rats; Journal of Pharmaceutical Sciences; vol. 62, No. 9, Sep. 1973; pp. 1455–1460.

*Primary Examiner*—Zohreh Fay
(74) *Attorney, Agent, or Firm*—Leonard Bloom

(57) ABSTRACT

Low potency, preservative free sterile topical anti-inflammatory steroid compositions are to be applied to the area surrounding the eye. The compositions involve, for example, sterile gauze pads in a sterile package, as well as single-use capsules and tubes for dispensing the medicinal composition.

4 Claims, No Drawings

LOW POTENCY UNPRESERVED STERILE TOPICAL CORTICOSTEROID COMPOSITIONS FOR DERMATITIS

FIELD OF THE INVENTION

The herein disclosed invention finds applicability in ophthalmology and dermatology. More specifically, the invention relates to compositions for application to inflamed tissue surrounding the eye.

BACKGROUND OF THE INVENTION

Pruritic, inflamed eyelids are a common clinical presentation to the dermatologist and ophthalmologist. Common causes of eyelid dermatitis are atopic dermatitis, contact dermatitis, contact urticaria, seborrheic dermatitis and psoriasis. An important treatment for each of these conditions is the use of topical corticosteroids. The ideal formulation for eyelid dermatitis treatment is not currently available.

Several ophthalmic ointments are disclosed in Chemical Abstracts:

Sirbu et al—Chemical Abstracts Vol. 100: abstract 56870; (1982) discloses a veterinary ophthalmic ointment for treating keratconjunctivitis containing hydrocortisone, lidocaine, lanolin and white petrolatum.

Dorsey—Chemical Abstracts Vol. 110 abstract 121459e (1989) shows a corticosteroid composition containing a corticosteroid, peppermint oil, urea, lanolin, propylene glycol and petrolatum used to treat eczematous dermatitis.

Tuomi et al—Chemical Abstracts Vol. 114 abstract 192384v (1990) teaches corticosteroid formulations containing hydrocortisone and propylene glycol creams.

Zilberman et al—Chemical Abstracts Vol. 84 abstract 140734b teaches an eye ointment containing hydrocortisone, kanamycin, lanolin and petrolatum, paraffin and paraffin oil.

Maistrello et al—Chemical Abstracts Vol. 80 abstract 22968a (1974) teach corticosteroids for application to the eye.

While the prior art teaches the application of corticosteroids to the eye, the prior art fails to teach sterile, non-preserved low potency corticosteroid ointments applied to the eye.

The inventors do not profess to be the first to dispense a sterile medication, for example, sterile ampoules are conventional dispensing means. However, the invention is directed to the novel means of applying for dermatitis of the eye a single dosage lower potency steroid ointment in a sterile preservative free ointment base.

SUMMARY OF THE INVENTION

This invention has as an object the preparation of ophthalmic ointments which do not inflame the delicate tissue surrounding the eye.

Another object is the preparation of ophthalmic ointments which do not produce an allergic response.

A further object is to produce simple formulations of sterile, preservative-free lower potency corticosteroid ophthalmic ointments.

A further object is to produce an easy to package and easy to use ophthalmic composition.

A still further object of this invention is to produce a sterile, preservative-free low-potency topical steroid ophthalmic product.

These and other objects of the present invention will become apparent from a reading of the following specification.

This invention contemplates the use of lower potency anti-inflammatory steroids. Steroid compositions have been rated on a scale of 1 to 7, with 7 being the least potent. (In this regard see Cornell and Stoughton, Dermatol. Clin. Vol. 2 (1984), pages 397–409 and Stoughton and Cornell, Semin. Dermatol Vol. 6 (1987, pages 72–76). The fluorinated steroids are generally rated among the most potent steroids, for example, Betamethasone and Clobetasol. Among the least potent steroids are non-fluorinated steroids, for example, desonide, cortisone, hydrocortisone, hydrocortisone butyrate, hydrocortisone valerate and aldomethasone diproprionate.

Because the skin around the eye is sensitive, non-fluorinated steroids will be used because fluorinated steroids would tend to adversely affect the skin around the eyes.

At times, higher concentrations of steroids may unduly irritate the skin around the eye and lower concentrations of steroid, e.g., 1% or even less, are at times contemplated by this invention.

In its broadest sense the disclosed invention is directed to a lower potency, preservative free anti-inflammatory steroid in a simple ointment base. The composition is designed to be therapeutically effective, while at the same time minimizing or eliminating any potential adverse side effects; particularly the skin around the eyes.

The anti-inflammatory steroids of this invention are classes 3–7 and preferably 4–7 topical steroids. The super fluorinated steroids (classes 1 and 2) tend to be too potent and irritating to the eye. In addition, super fluorinated steroids (classes 1 and 2) are not desirable for use because these steroids, after long use, tend to cause cataracts and accelerate glaucoma.

The thin structure of the eyelid and proximity to the eye make higher potency (super fluorinated) steroids less than ideal for the treatment of eyelid dermatitis. Further, high potency steroids increase the risk to the skin, for example, thinning and atrophy. In addition, high potency steroids increase the risk to the eye of cataract formation and glaucoma. Preserved medications increase the risk of both contact allergy and direct toxic effects to the eyelid and the eye. Currently available commercial preparations of corticosteroid ointments marketed for ophthalmic use, are not preservative-free, and are all generally high potency fluorinated steroids. Commercial dermatologic preparations, while available as low potency non-fluorinated corticosteroid are preserved and non-sterile.

Among the prescribed corticosteroid ophthalmic ointment preparations are dexamethasone sodium phosphate (AK-Dex by Akorn Pharmaceuticals, Decadron Sterile Ophthalmic Petrolatum by Merck and Maxidex by Alcon) and fluoromethalone ophthalmic ointment (FML S.O.P. by Allergan). The above ophthalmic preparations are fluorinated. (See the Ophthalmic PDR, 1995)

Dermatologic formulations available as low potency non-fluorinated corticosteroids include various strengths of hydrocortisone base or acetate, which are all non-sterile and preserved. These and other low potency topical steroid preparations are listed in the Monthly Prescribing Reference, January 1996. The current invention is intended to overcome the shortcomings of the presently available corticosteroid formulations.

The current invention would fulfill an important niche for some of the more common oculo-dermal problems confronting both the ophthalmologist and dermatologist, as well as the primary care physician. The present invention is expected to provide a new therapeutic modality for the clinician.

There exists a major crisis in topical formulation of corticosteroids for the treatment of acute and chronic diseases of the skin around the eyes. There is no preservative free, hypoallergenic, sterile preparation available to treat common and uncommon dermatosis present in the periocular region. The concern is that the periocular or eyelid skin is one of the thinnest, and most sensitive areas of the human body and cannot withstand currently available commercial topical corticosteroid formulations as they contain noxious preservatives and alcohols that adversely affect the very condition that is to be treated. In addition to the lack of preservative free topical steroids for periocular use, there are no pure topical steroids that are sterile. Dermatitis, such as seborrheic dermatitis (a very common disorder currently treated), if treated with the currently commercially available preparations could induce an irritant affect due to their preservatives or introduce an infection into the eye due to their non-sterile nature.

The skin of the eyelids is the thinnest in the body as described in Ophthalmology Principles and Concepts— author F. W. Newell—fourth edition—1978—(pages 49 and 50)The C. V. Mosby Company.

The inventors have found that, in view of the special sensitivity of the skin around the eye, a particularly mild ointment, based together with a low potency steroid preparation provide the ideal vehicle and medicament for application to the skin around the eye. In view of the particular sensitivity of the skin around the eye to allergic influences, the disclosed invention avoids the use of preservatives. Because of skin-sensitivity around the eye, applicants have limited the number of additional medicaments or adjuvants in the ointment composition to avoid introducing onto the skin agents which would produce an allergic or other type of irritating reaction on the skin. Accordingly, applicants' composition is preservative-free. Applicants have sterilized their topical composition to avoid the introduction of harmful infectious agents from the topical composition onto the sensitive skin area around the eye. The final composition embodies only a minimal number of components, namely, active ingredient and simple carrier vehicle.

Ellis in Ocular Therapeutics and Pharmacology—sixth edition (1981) the C. V. Mosby Co., page 93, teaches the application of a corticosteroid ointment to the eyelids. Ellis fails to realize the need for a sterile product; does not disclose that the ointment base is petrolatum and does not recognize the need for a lower potency steroid to be used.

American Drug Index 1989—(33$^{rd}$ edition) page 466, teaches hydrocortisone 2.5% in a white petrolatum base. This product was not intended for application to the eye-lids or the skin around the eye and, further, there was no provision for using this ointment in the sterile state. This product is no longer on the market.

There are many methods to assess systemic activity or local anti-inflammatory activity. By far the most predictive test has been the vasoconstrictor assay, which is performed on the skin of human volunteers. When a topical steroid is applied to the skin, blanching will occur 4 to 7 hours after the application, and the area will remain blanched for 8 to 48 hours, even after the steroid has been thoroughly washed from the surface. Thus, six to eight compounds can be applied to the flexural areas of the forearms simultaneously and compared against each other based on the degree of blanching.

In another test, stripped skin, which develops erythema, was shown to develop blanching when hydrocortisone was applied. Thus, skin made erythematous with nicotinate ester could be restored to normal color by treating with a glucocorticosteroid. These two methods of evaluating the vasoconstrictor ability of steroids are somewhat more complicated and costly than simply applying the agent to the mitotic normal forearm skin of human volunteers. Suppression of the mitotic index and atrophogenic potential measure primarily antiproliferative effects and are not yet used as routinely as the vasoconstrictor assay.

TABLE 1

Ranking of Topical steroids for Psoriasis*

| | BRAND NAME | GENERIC NAME |
|---|---|---|
| I. | Diprolene ointment 0.05% | Betamethasone dipropionate in optimized vehicle |
| II. | Cyclocort ointment 0.1% | Amcinonide |
| | Diprosone ointment 0.05% | Betamethasone dipropionate |
| | Florone ointment 0.05% | Diflorasone diacetate |
| | Halog cream 0.1% | halcinonide |
| | Lidex cream 0.05% | Fluocinonide |
| | Lidex ointment 0.05% | Fluocinonide |
| | Maxiflor ointment 0.05% | Diflorasone diacetate |
| | Topicort cream 0.25% | Desoximethasone |
| | Topicort ointment 0.25% | Desoximethasone |
| | Topsyn gel 0.05% | Fluocinonide |
| III. | Aristocort cream (HP) 0.5% | Triamcinolone acetonide |
| | Diprosene cream 0.05% | Betamethasone dipropionate |
| | Florone cream 0.05% | Diflorasone diacetate |
| | Maxiflor cream 0.05% | Diflorasone diacetate |
| | Valisone ointment 0.1% | Betamethasone valerate |
| IV. | Aristocort ointment 0.1% | Triamcinolone acetonide |
| | Benisone ointment 0.025% | Betamethasone benzoate |
| | Cordran ointment 0.05% | Flurandrenolide |
| | Kenalog ointment 0.1% | Triamcinolone acetonide |
| | Synalar cream (HP) 0.2% | Fluocinolone acetonide |
| | Synalar ointment 0.025% | Fluocinolone acetonide |
| | Topicort LP cream 0.05% | Desoximethasone |
| V. | Benisone cream 0.025% | Betamethasone benzoate |
| | Cordran cream 0.05% | Flurandrenolide |
| | Diprosone lotion 0.02% | Betamethasone dipropionate |
| | Kenalog cream 0.1% | Triamcinolone acetonide |
| | Kenalog lotion 0.1% | Triamcinolone acetonide |
| | Laced cream 0.1% | Hydrocortisone butyrate |
| | Synalar cream 0.025% | Fluocinolone acetonide |
| | Valisone cream 0.1% | Betamethasone valerate |
| | Valisone lotion 0.1% | Betamethasone valerate |
| | Westcort cream 0.2% | Hydrocortisone valerate |
| VI. | Tridesilon cream 0.05% | Desonide |
| | Locorten cream 0.03% | Flumethasone pivalate |
| | Synalar solution 0.01% | Fluocinolone acetonide |
| VII. | Topicais with hydrocortisone, dexamethasone, flumethalone, prednisolone and methyl prednisolone | |

*Group 1 is the most potent, and potency descends with each group to Group VII, which is least potent. There is no significant difference of agents within any given group; within each group the compounds are arranged alphabetically.

The potencies and rating scale of ophthalmic steroid ointments has been established as an index and is well known to those skilled in the art. The steroid ointments have been indexed in the Monthly Prescribing Reference January 1996, page 66 (Prescribing Reference, Inc., 53 Park Place, New York, N.Y.). Another example of ophthalmic steroid ointment rating is to be found in Dermatologic Clinics—Vol. 2, No. 3, July 1984, pages 397–409 (399) article by Cornell et al. Tests for determining steroid potency are described by Schlagel et al in P.S.E.B.M. Vol. 101 (1959) pages 629–632.

The invention involves the development of a topical corticosteroid for opthalmological and dermatological use that is sterile, hypoallergenic, preservative-free and will range in strength from class 2–7 and preferably 3–7 topical steroids. See the above ranking of topical steroids with specific brand names listed, as well as generic names, and class of potency with class 2 being most potent and class 7 being least potent.

There currently is a class 2 sterile ophthalmic topical steroid but it is not preservative free and is unavailable in a pure form, i.e., it is combined with a topical antibiotic.

The formulation that this invention anticipates will encompass all strengths of class 2 through class 7 and preferably 3–7 topical steroids mixed with petrolatum, white petrolatum, or mineral oil; ointments or lotions, gel base; and compositions impregnated on a cotton gauze and sealed in a foil or comparable air-tight hermetically sealed wrap that is sterilized via gamma radiation. In addition, the steroid compositions of this invention could be supplied in single use sterile dropper capsules. Tubes and preferably single dose tubes of mediation are contemplated by this invention.

The foil wrapped formulation will be most convenient. The invention anticipates each wrapper to be a single treatment. This will insure maximal sterility, since after each treatment the spent gauze medication and wrapper will be discarded and a fresh medication in a new wrapper will be used for the next treatment. For treatment of irritant or contact dermatitis, for example, treatment with topical corticosteroids will typically be twice daily, for two weeks, so that one dispensing package will optimally contain 28 to 30 dosage wrappers to complete the full course of therapy.

Methods for sterilizing ointments are taught by Reveley in U.S. Pat. No. 3,348,905. In that patent an ointment impregnated gauze is packaged; and by a process using heat and water inside the sealed package, the gauze-containing ointment is sterilized.

Examples of ophthalmologic and dermatologic diseases to be treated by the compositions of this invention are: contact dermatitis, irritant dermatitis, seborrheic dermatitis, psoriasis vulgaris, blepharitis, granuloma annulare, mycosis fungoides, necrobiosis lipoidica, pityriasis lichenoides et varioliformis accuminatum, lymphomatoid papulosis, erythema annulare centrifugum, photodermatitis, lupus erythematosis, phytophotodermatitis, plant dermatitis, and eczematous dermatitis, to name but a few.

Recently a new disease has been described called the "Localized Eye Area Sensitivity Syndrome". This disease was reported by Stephens T J et al in 1990 (see attached paper describing condition with all appropriate references). This disease demonstrates the irritancy potential of topical preparations around the eyes and clearly indicates the need for the invention described herein. There is a definite urgency for the development of the invention, since it is needed for patients with ophthalmologic and dermatologic dermatosis in the region of the eye and within the eye. Localized Eye Area Sensitivity Syndrome (LEASS) has been described as a collection of both subjective and objective symptoms which occur when susceptible individuals apply topical products containing certain chemicals to the periorbital area.

The first report of Localized Eye Area Sensitivity Syndrome (LEASS) was published in 1990. (Stevens et al, J. Toxicol Cut Ocul Toxicol Vol. 8, NO. 4 [1990] pages 569–570) Women in cosmetic testing programs complaining of this syndrome; report itching, burning, stinging and watering of the eyes, to what they perceive as foreign body sensations in the eye. Ophthalmologic examinations reveal bulbar conjunctival chemosis with ocular surface changes not observed. Dermatologic examinations reveal only erythematous skin. The publication Practicing Dermatologist has reported LEASS. This syndrome (LEASS) was referenced in a presentation at the 1996 annual meeting of the American Society of Contact Dermatitis meeting in Washington, D.C. and in a different presentation at the 1996 annual meeting of the American Academy of Dermatology in Washington, D.C.

These principle characteristics of Localized Eye Area Sensitivity Syndrome (LEASS) are as follows:
Anatomical Specificity
Periorbital Area
No Ocular Surface Reactions
Cannot Be Duplicated on the Skin of the Arm or Back by Patch Testing
Subjective Symptoms
Foreign Body Sensation in the Eye
Watering of the Eyes
Objective Symptoms
Observable Tearing of the Eyes
Erythematous Periorbital Skin
Chemosis and Injection
Hive Like Appearance of the Periorbital Area While it is rare that a new syndrome is identified, however, LEASS clearly qualifies as a new syndrome. It is evident that both scientists and physicians are in the rudimentary stages of understanding the interactive nature of both objective and subjective sensory cutaneous and ocular reactions.

The ideal formulation as contemplated by this invention would be an unpreserved, low-potency (non-fluorinated steroid) sterile ointment. Compositions contemplated by the present invention are directed to 1%, 2.5% and 5% hydrocortisone in a sterile petrolatum-mineral oil unpreserved vehicle. Other low potency corticosteroids could be used including aldomethasone 0.05%, aldomethasone dipropionate, the intermediate potency corticosteroid desonide at 0.05%, hydrocortisone butyrate and hydrocortisone valerate at lower concentrations. The concentrations of steroid as herein set forth are viewed as effective amounts for the intended use. The concentrations may vary based on patient need bearing in mind the need to use lower potency steroids.

The disclosed invention centers around an ophthalmic topical composition comprising a sterile, hypoallergenic, preservative-free, lower potency corticosteroid, in a petrolatum base contained in a sterile dispensing container.

Medicated, packaged gauze products are of advantage over the ophthalmic ointments dispensed from a tube in that the product in the tube, once the tube is opened is no longer sterile. Applicant's product contained in a gauze packet maintains its sterility.

Besides mineral oils, vegetable oils can be used in the formulations. Examples of vegetable oils are peanut oil and olive oil. Other vegetable oils well known to those skilled in the art would be operative.

Examples of effective formulations contemplated by this invention are:

EXAMPLE 1

Triamcinolone acetonide 0.1% in mineral oil vehicle

EXAMPLE 2

Betamethasone benzoate 0.025% in petrolatum vehicle

EXAMPLE 3

Hydrocortisone butyrate 0.1% in mineral oil vehicle

EXAMPLE 4

Desonide 0.05% in mineral oil vehicle

EXAMPLE 5

Hydrocortisone valerate 0.1% in a mineral oil emulsion vehicle

EXAMPLE 6

Betamethasone benzoate 0.025% in an olive oil vehicle

These compositions are to be dispensed in a single dose preservative free sterile package.

These formulations can be formulated onto gauze applicators in sterile packages. They can also be incorporated into single dose applicator capsules or tubes.

In its broadest aspect this invention is directed to an ophthalmic topical composition comprising a sterile, hypoallergenic, preservative-free, lower potency corticosteroid, in a petrolatum base contained in a sterile dispensing container. This dispensing container can be a sterile dispensing container, e.g., a foil packet. As another embodiment a corticosteroid can be incorporated into petrolatum contained on a sterile gauze pad which in turn is in a sterile wrapper. The sterile corticosteroid compositions of this invention can be dispensed in a single dose eye drop capsule and tubes, preferably a single-use tube.

A broad aspect of this invention envisions a method for treating localized dermatitis of the eye area comprising applying to the eye area of a patient with localized dermatitis of the eye a sterile, preservative-free composition containing an effective amount of a lower potency anti-inflammatory steroid in a mineral oil, vegetable oil or petrolatum base dispensed from a sterile single dose container. The anti-inflammatory steroid can be non-fluorinated and be present in the topical composition in an amount of less than 1%.

The herein disclosed invention further contemplates a method for treating Localized Eye Area Sensitivity Syndrome (LEASS) comprising applying to the eye area of a patient with such a syndrome a sterile, preservative-free composition containing a lower potency anti-inflammatory steroid in a petrolatum base. Specifically, the composition can be applied using a gauze pad.

In summary, the problems solved by applicants and not recognized by the prior art are that:

1) Applicants have produced a ophthalmic ointment which does not produce an allergic response or adverse side effects because the limited number of ingredients contained in the ointment composition therein is limited.

2) The ointment is preservative free because preservatives are liable to produce an allergic response and particularly on the skin area surrounding the eye.

3) The ointment has a low-potency topical steroid, because a high potency steroid is likely to react adversely on the delicate skin around the eyes.

4) The product is dispensed in a single dose package so sterility is maintained.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A method for treating localized dermatitis of the eye area consisting essentially of applying to the eye area of a patient with localized dermatitis of the eye a sterile, preservative-free composition containing an effective amount of a lower potency anti-inflammatory steroid in a mineral oil, vegetable oil or petrolatum base dispensed from a sterile single dose dispensing container.

2. The method of claim 1 wherein the anti-inflammatory steroid is non-fluorinated.

3. The method of claim 2 wherein the concentration of the non-fluorinated steroid is less than 1%.

4. The method of claim 1 wherein the lower potency anti-inflammatory steroid is contained in petrolatum base.

\* \* \* \* \*